United States Patent [19]

Steck et al.

[11] 4,302,459

[45] Nov. 24, 1981

[54] LIPOSOME CARRIERS IN LEISHMANIASIS CHEMOTHERAPY WITH 8-AMINOQUINOLINE DERIVATIVES

[75] Inventors: Edgar A. Steck, Silver Spring, Md.; Carl R. Alving, Washington, D.C.

[73] Assignee: The United States of America as represented by the Secretary of the Army, Washington, D.C.

[21] Appl. No.: 131,576

[22] Filed: Mar. 19, 1980

[51] Int. Cl.³ .............................................. A61K 31/47
[52] U.S. Cl. .................................. 424/258; 424/199; 424/245; 424/365
[58] Field of Search ................ 424/365, 258, 199, 245

[56] References Cited

U.S. PATENT DOCUMENTS 4,016,290  4/1977  Rahman .............................. 424/199
4,224,179  9/1980  Schneider .......................... 424/199

OTHER PUBLICATIONS

Alving et al.—Chem. Abst. vol. 91 (1979) p. 162, 911d.
Alving et al.-Chem. Abst. vol. 89 (1978)pp. 140, 460n.

*Primary Examiner*—Sam Rosen
*Attorney, Agent, or Firm*—William G. Gapcynski; Werten F. W. Bellamy

[57] ABSTRACT

An improved method is provided for the chemotherapy of leishmanial infections. An 8-aminoquinoline anti-leishmanial agent is encapsulated within liposomes and the liposome-encapsulated drug is injected into the body. Subject use of a liposome carrier has produced marked enhancement of the effectiveness of the drug against leishmanial parasites in the liver (such as characteristic of infections which are difficult to treat).

17 Claims, No Drawings

LIPOSOME CARRIERS IN LEISHMANIASIS CHEMOTHERAPY WITH 8-AMINOQUINOLINE DERIVATIVES

The invention described herein may be manufactured and used by or for the Government for governmental purposes without payment of any royalty thereon or therefor.

BACKGROUND OF THE INVENTIONS

The invention generally relates to the chemotherapy or treatment of leishmaniasis. Leishmania are well known intra-cellular protozoan parasites which may give rise to serious infections in man. The organisms are transmitted by the "bite" of an infected sandfly, and invade the reticulo-endothelial system (RES). The parasites are highly successful in their ability to grow and multiply in the very tissues of the vertebrate host which are responsible for reaction to invading organisms. Expectedly, such location of Leishmania renders difficult a satisfactory approach to chemotherapy, and there is highly complex inter-play between parasites and cellular immune responses of the host. In the RES, the parasites lie within the host macrophage for at least part of their life cycle. Fusion of host cell secondary lysosomes with the parasitophorous vacuoles apparently occurs without preventing subsequent multiplication of the Leishmania. Such fusion may provide means for access for nutrients to the parasite, but also exposes the parasite to host antibodies and lysosomal enzymes. In man, the result of successful invasion of the spleen and liver by Leishmania donovani most frequently is death. Scarring of the skin may be the sole manifestation of infection with Leishmania tropica and allied dermatotropic organisms (as, Leishmania aethiopica, L. mexicana, L. peruviana, and L. guyanensis). Intermediate in severity are invasions of muco-cutaneous tissues by Leishmania braziliensis. There are considerable differences among various animals in their response to leishmanial infections, however, a satisfactory animal model for laboratory trials has been found in Leishmania donovani infections in the golden hamster.

The L. donovani-hamster model has been used widely to assess candidate drugs for anti-leishmanial effects. Unfortunately, relatively few drugs have been found to show appreciable activity on screening, and fewer yet have merited trail in man. Antimony drugs are a mainstay for treatment despite evaluation of diverse types both in the laboratory and in clinical trails. Pentavalent compounds of antimony are better tolerated than trivalent antimonials, yet severe toxic side effects may occur, in particular, among poorly nourished patients. Toxicity of such drugs may affect the liver (hepatitis), kidneys (nephritis), or the heart (myocarditis). Of these toxic effects, myocarditis is the greatest and most common problem. Of the antimonial drugs, one widely used in the clinic is the N-methyl glucamine salt of antimonic acid, frequently called meglumine antimoniate. That compound has been presently employed as a reference drug in evaluation of compounds in the L. donovani-hamster test.

Quinoline derivatives are known to have chemotherapeutic effects against diverse parasites of man. Especially noteworthy potency against malaria parasites has been demonstrated among 4-aminoquinoline and 8-aminoquinoline structures. In the instance of 8-aminoquinoline derivatives, but not 4-aminoquinolines, anti-leishmanial effects have been demonstrated in the Leishmania donovani test in the hamster. Such activity against Leishmania shown by the 8-aminoquinolines is a distinct aspect of anti-parasitic effects, and not related to (e.g.) antimalarial profile thereof. Among series of 8-aminoquinolines, certain 8-amino-6-methoxy-4-methylquinolines (otherwise called 8-amino-6-methoxylepidines) have been identified as markedly more effective than allied compounds lacking the 4-methyl grouping: K. E. Kinnamon, et al., Am. J. Trop. Med. Hyg., 27, 751-757 (1978). The 8-amino-6-methoxylepidines are also subject of the co-pending U.S. Patent application Ser. No. 886,024 (Mar. 13, 1978) of K. E. Kinnamon. In such work, meglumine antimoniate was used as reference drug. Activity was expressed through use of G index derived from the expression $$G \text{ index} = \frac{SD_{90} \text{ for meglumine antimoniate}}{SD_{90} \text{ for test compound}}.$$

wherein $SD_{90}$ refers to the dose causing 90% suppression of L. donovani parasites (amastigote form) present in the livers of infected hamsters. Under standard test conditions—as described by W. L. Hanson, et al. in International J. Parasitol., 7, 443-447 (1977)—primaquine (which is the drug of choice as a radical curative antimalarial agent) had G index=2.1; 4-methyl primaquine had G index=33. The most active compound was 8-(6-diethylaminohexylamino)-6-methoxylepidine, which had G index=474 by intramuscular route and 708 by oral route. 8-Aminoquinolines have thus been established as effective anti-leishmanial agents in a standard test system. Unfortunately, such series has definite liabilities in toxic side effects. The common denominator in the toxicity profile of 8-aminoquinolines involves red blood cells, including events which may lead to acute hemolytic crises in various people having G-6-PD deficiency in their erythrocytes.

Liposomes are defined as closed vesicles, or sacs, which contain phospholipids (examples of which are lecithin and sphingomyelin) and which may contain other lipids (examples of which are cholesterol and other sterols or steroids; charged lipids such as dicetyl phosphate and octadecylamine; glycolipids; and also lipid-soluble vitamins). When shaken in the presence of water, with the water being at least 50% (w/w) compared to phospholipids, thin films of such lipid mixtures are spontaneously formed into discrete particles consisting of concentric spherical shells of lipid bilayer membranes which are separated by aqueous interspaces. These are referred to as multilamellar liposomes (MLL). Upon sonication, the MLL are converted to small unilamellar liposomes (ULL). It was first demonstrated that the MLL vesicle membranes were completely closed and did not allow escape of a marker compound present in the aqueous interspaces; similar properties later were found for ULL.

Numerous studies have shown that liposomes, upon injection into animals and man, are taken up rapidly by cells, and intracellular lysosomes, of the RES, particularly those in the liver. Because of the relative impermeability of liposomes, and speedy removal of them from the circulatory system, substances in the aqueous interspaces of liposomes remain concentrated therein and are unexposed to plasma. These characteristics of liposomes suggested that they might have a potential for application as carriers for anti-leishmanial agents, as 8-aminoquinoline drugs. The cells and tissues in which the liposomes are readily taken up are the very locations in which the Leishmania organisms predominantly reside, thus raising the possibility that liposomes might carry concentrated doses of those agents directly to organisms residing within retriculoendothelial cells of the spleen and liver. Not only would the drugs be directed more effectively to tissues and cells harboring the obligate intracellular Leishmania, but also the encapsulated drugs would have decreased liability for producing toxic side-effects through exposure to blood. Moreover, there would be strong probability for prolonged effectiveness of the drug through slow biodegradation of the multilamellar membrane structure of the liposomes.

SUMMARY OF THE INVENTION

The present invention relates to a novel technique in the treatment of leishmaniasis, consisting in the incorporation of an anti-leishmanial 8-aminoquinoline derivative into liposomes, and introduction of the "encapsulated" agent into the body of an infected mammal. By this procedure, the effectiveness and duration of action are prolonged, and also drug toxicity is decreased. As specific embodiment of the invention, use of 8-aminoquinolines in liposome carriers has been found to provide improved therapy of leishmaniasis owing to increased effectiveness, prolonged duration of action, and lessened liability to toxicity of the drug. Specifically, we have centered attention upon use of primaquine and 8-(6-diethylaminohexylamino)-6-methoxylepidine as representative 8-aminoquinolines.

Further aspects of the present invention will become apparent upon assessment of the detailed description of the specific embodiments of the novel approach to the therapy of leishmaniases.

DETAILED DESCRIPTION OF THE INVENTION

Primaquine diphosphate has been shown (K. E. Kinnamon, et al., loc. cit.) to have modest anti-leishmanial effects in a standard test system (cf. W. L. Hanson, et al., loc. cit.) in which 8-(6-diethylaminohexylamino)-6-methoxylepidine dihydrochloride was outstandingly effective. Each of those 8-aminoquinolines can be encapsulated in liposomes as shown in instant invention. That was achieved by drying an appropriate lipid mixture in a thin film and introducing an aqueous solution of primaquine salt (e.g., the diphosphate) or of a salt of 8-(6-diethylaminohexylamino)-6-methoxylepidine (as, its dihydrochloride) in such manner as to produce liposomes containing the appropriate drug. The carrier system for introducing the anti-leishmanial agent into the animal afforded means for enhancing effectiveness of the drug against *Leishmania donovani* infections in a model test system, as hitherto described.

EXPERIMENTAL

Herein are offered examples to provide methods for illustrating the invention, and do not limit its scope in the treatment of leishmanial infections. Representative phospholipids which may be used in preparing the liposomes include lecithin, β, γ-dipalmitoyl-α-lecithin (as well as related β, γ-disubstituted α-phosphatidyl choline types), sphingomyelin, and the like. The steroidal component enhanced the stability of the liposomes, and was selected from conveniently available compounds such as cholesterol, lanosterol, cholestanol, and the like.

The liposomes were rendered charged by addition of readily accessible, appropriate lipid soluble compounds.

All temperatures not otherwise indicated are in degrees Celsius (°C.). All parts or percentages are given on weight basis.

MATERIALS

For convenience in preparation of liposomes, stock solutions of phospholipids, cholesterol, and charged component were prepared in chloroform and stored at −20°. Commercial normal saline for intravenous injections was the 0.154 M sodium chloride solution here used. Meglumine antimoniate was a commercial sample of Glucantime ®; duplicate antimony determinations were done on the sample as used. Values found were 25.49% and 25.62% antimony. The commercial sample of primaquine diphosphate was 99.0% pure. 8-(6-Diethylaminohexylamino)-6-methoxylepidine dihydrochloride was 99.4% pure.

METHODS

Assessment of anti-leishmanial effects was done in a model test system based on work of Stauber, et al. [J. Protozool., 5, 269–273 (1958)] and which has been improved in design recently (W. L. Hanson, et al., loc. cit.).

Male golden hamsters (*Mesocricetus auratus*), weighing approximately 50–60 gm and the Khartoum strain of *Leishmania donovani* were used in this work. Suspensions of amastigotes for the inoculation of experimental hamsters were prepared by grinding heavily infected hamster spleens in Hanks' balanced salt solution in a Ten Broeck tissue grinder and diluting the suspension to contain $10^7$ amastigotes per 0.2 ml, the amount inoculated into each hamster via the intracardial route. Administration of the drum was initiated at selected intervals (as, 3 days, or 17 days) after infection and continued once daily for 4 days. One day after halt of therapy, the hamsters were weighed, killed, their livers removed and weighed. Liver impressions were prepared, stained with Giemsa's stain and the ratio of the number of amastigotes per host liver cell nucleus determined.

In preparation for the initiation of therapy, the hamsters were weighed and apportioned into groups of 6 to 11. Solid standard compound, meglumine antimoniate, was prepared in 0.1% Tween ® 80 plus 0.5% hydroxyethylcellulose (HEC-Tween ®) formulation, and administered daily on days 3 through 6 via the intra-cardial route. The reference compound was administered at dose levels of 104, 13, and 3.25 mgm per kilo per day to the hamsters. Test samples of liposomes containing primaquine diphosphate or 8-(6-diethylaminohexylamino)-6-methoxylepidine dihydrochloride were injected at dose levels of 104, 13, and 3.25 mg. kg/day. A group of 6 hamsters was the minimum used for each dosage level.

Comparison of the suppressive effects of the various liposome preparations with that of the meglumine antimoniate in HEC-Tween ® was made from parasite densities in the liver of each hamster. The total number of parasites in the liver of each hamster was determined from liver impressions according to the method of Hanson et al. (loc. cit.).

When the ratio of the number of amastigotes to the number of liver cells had been determined for each hamster in all experimental groups, these data along with initial and final body weights were evaluated with the aid of an IBM 360 computer. A program was devised in which the raw data were accepted by the computer and the total and mean numbers of amastigotes per liver, percent suppression of numbers of amastigotes, and percent body weight change were calculated. Significant tests on the percent suppression of amastigotes were done. The calculations allowed a comparison of the total number of amastigotes in the liver of each hamster receiving the reference preparation or liposome compositions (containing the 8-aminoquinoline derivative) with the mean number of amastigotes in the livers of controls.

A comparison of anti-leishmanial activity of each liposome sample was made with the reference formulation of meglumine antimoniate in HEC-Tween ®. The drug dosage levels of liposome-encapsulated samples required for a given degree of effect such as 90% suppression ($SD_{90}$) was estimated graphically by plotting on log paper the percent parasite suppression vs. milligrams of compound administered per kilogram body weight of the hamster.

The percentage weight gain or loss of treated animals was used as a crude indication of toxicity. In addition, the hamsters were observed daily for clinical signs of toxicity such as roughened hair coat, nervous disorders and death. At necropsy, gross lesions were noted. All of these criteria were used in assessing any toxicity of the test composition.

The relatively high degree of reproducibility of the screening procedure is apparent in the following data. After 39 weekly experiments, the mean number of amastigotes in the livers of control hamsters was found to be $5.11 \times 10^8$ ($\pm 10^7$, at 95% confidence). Equally good reproducibility was obtained from hamsters receiving 104, 13, or 3.25 mg/kg of the reference compound, meglumine antimoniate. The mean number of amastigotes in the livers of these hamsters were $12.1 \times 10^7$ ($\pm 1.1 \times 10^6$), $1.57 \times 10^8$ ($\pm 11.6 \times 10^6$) and $3.4 \times 10^8$ ($\pm 1.39 \times 10^9$). These represent suppressions 97.6%, 69.2% and 38.3%, respectively, for the three drug dosage levels.

EXAMPLES

Example 1: Primaquine diphosphate: Neat drug

In the standardized test system [Stauber, et al., and Hanson, et al., loc. cit.], the anti-leishmanial activity of primaquine diphosphate was shown to be 2.1 times that of meglumine antimoniate (G index, 2.1) against a 3 day infection of *Leishmania donovani* in hamsters [Kinnamon, et al., loc. cit.]. When tested in 17 day infections, primaquine diphosphate gave evidence of activity at $G \sim 1.5$.

Example 2:
8-(6-Diethylaminohexylamino)-6-methoxylepidine dihydrochloride: Neat drug 8-(6-Diethylaminohexylamino)-6-methoxylepidine dihydrochloride (also known as WR-6026 in files of compounds at Walter Reed Army Institute of Research) had markedly greater effectiveness than meglumine antimoniate in the standardized 3 day test against *L. donovani* infections in hamsters (loc. cit.). When compared with the standard drug [Kinnamon, et al., loc. cit.], the WR-6026 showed G index 474 by intramuscular route and 708 by oral route.

WR-6026 was now further assessed against 17 day infections of *L. donovani* in hamsters, using the intramuscular route for administration. The G index was 161.

Example 3:
8-(6-Diethylaminohexylamino)-6-methoxylepidine: Encapsulation in negative liposomes Chloroform solutions of dipalmitoyl phosphatidylcholine, cholesterol, and dicetyl phosphate were prepared. Portions of each were mixed in such way that there were molar ratios of 2/1.5/0.22. The mixture was placed in a pear-shaped flask, and the solvent removed in vacuo on a rotary evaporator. There resulted an homogeneous film of lipid, which was further dried under high vacuum. To that there was added a small amount of 0.5 mm glass beads, followed by sufficient aqueous 0.308 M solution of WR-6026 so that the phosphatidylcholine content of the final aqueous dispersion was 10 mM. The liposomes were swollen by shaking for several minutes on a vortex mixer, and then freed of untrapped 8-aminoquinoline derivative by diluting in 10 volumes of 0.15 M sodium chloride solution and centrifuging at 20 200 g for 10 minutes at 22°. Each pellet was suspended in 0.15 M sodium chloride solution in half of the original aqueous volume. The resulting liposomes were injected into *L. donovani*-infected hamsters.

Analysis of an aliquot of the washed liposomes was done to ascertain the amount of WR-6026 trapped in the vesicles. The liposomes were disrupted and lipids removed by shaking the portion with an equal volume of chloroform. The aqueous phase and water washings of the chloroform layer were combined and adjusted to pH ($1.73 \pm 0.04$) with 0.1 N HCl. Absorption measurements were made at 262.5 and 275 nm, and results were compared to reference value with 8-(6-diethylaminohexylamino)-6-methoxylepidine dihydrochloride. There was thus determined the extent of drug entrapped in the liposomes.

Direct comparison was made of the effects produced in Leishmania-infected hamsters (17 day infections) by intra-cardial administration of meglumine antimoniate alone and of WR-6026 incorporated in the negatively-charged liposomes. On the basis of definition that $SD_{50}$ is the amount of drug required to cause 50% suppression of parasites, in this experiment the $SD_{50}$ for meglumine antimoniate (neat) was 290 based on Sb. WR-6026 (neat) had $SD_{50}$ of 1.8 mgm/kg. The $SD_{50}$ for WR-6026 encapsulated in negative liposomes was 0.42 mgm/kg. Thus, the G index for neat 8-(6-diethylaminohexylamino)-6-methoxylepidine hydrochloride was 161, and that for the liposome-incorporated drug was 690.

Example 4:
8-(6-Diethylaminohexylamino)-6-methoxylepidine: Encapsulation in positive liposomes In a direct comparison with Example 3, positive liposomes were prepared containing 8-(6-diethylaminohexylamino)-6-methoxylepidine. After the manner described, stearylamine was used in place of dicetylphosphate, giving molar ratios of dipalmitoyl phosphatidylcholine, cholesterol, and stearylamine amounting to 2/1.5/0.22. Thereafter, the method of Example 3 was followed with formation of liposomes having WR-6026 entrapped therein.

Direct intercomparison of the preparation of the 8-aminoquinoline drug in positive liposomes was made with those described previously. Here, the $SD_{50}$ was found to be 0.22 mgm/kg, giving a G index of 1318.

Example 5:
8-(6-Diethylaminohexylamino)-6-methoxylepidine:
Encapsulation in neutral liposomes In direct comparison with Example 3 and Example 4, there were prepared neutral liposomes containing the 8-aminoquinoline drum WR-6026. This was done by admixing chloroform solutions of dipalmitoyl phosphatidylcholine and cholesterol in molar ratios of 2/1.5, and following the scheme outlined in Example 3.

Testing of the WR-6026 incorporated in neutral liposomes was done in direct comparison with the drug encapsulated in negative and positive liposomes. In this instance, the $SD_{50}$ for WR-6026 was 0.158 mgm/kg, giving a G index of 1835.

EXAMPLE 6

Primaquine: Encapsulation in liposomes

Primaquine diphosphate was incorporated in neutral liposomes, after the manner of Example 5. The assessment of anti-leishmanial effects was done in the standard way, repeatedly. Liposome-incorporated drug showed a variable level of effectiveness, despite extreme efforts at uniformity, otherwise clearly evident in direct comparisons. In many cases, the preparations containing primaquine gave erratic values, much in contrast to 8-(6-diethylaminohexylamino)-6-methoxylepidine (which has been designated as WR-6026). The Figure shows the results of comparing the anti-leishmanial effects of the two 8-aminoquinoline drugs when incorporated in liposomes. Efficacies of Primaquine Diphosphate and WR-6026, Encapsulated in Liposomes are illustrated. In a single experiment duplicate liposome preparations contained either primaquine diphosphate (closed symbols) or WR-6026 (open symbols).

Repetition of studies with primaquine in negatively-charged liposomes (cf. Example 3) and in positively-charged liposomes (cf. Example 4) also gave variable levels of anti-leishmanial effectiveness. In most instances, primaquine in liposomes was more effective than neat neglumine antimoniate, but uniformly less so than WR-6026 (whether encapsulated in liposomes or as the neat drug).

We claim:

1. The product prepared by a process for encapsulating an anti-leishmanial 8-aminoquinoline drug within liposomes comprising the steps of:
  a. drying a lipid mixture to form a dry film;
  b. wetting the lipid film with an aqueous solution of an 8-aminoquinoline drug;
  c. mixing the aqueous solution of an 8-aminoquinoline drug and lipid film to form a suspension of an 8-aminoquinoline drug encapsulated by liposomes;
  d. separating the liposome-encapsulated drug; and
  e. washing the liposome-encapsulated 8-aminoquinoline drug to remove substantially all nonencapsulated 8-aminoquinoline drug therefrom.

2. The product prepared by the process of claim 1 wherein the lipid is a bilayered mixture consisting of an admixture of phospholipid and cholesterol with or without a lipid which imparts an electrical charge to the admixture.

3. The product of claim 2 wherein the liposome-encapsulated 8-aminoquinoline drug is entrapped between the layers of the lipid.

4. The product of claim 2 wherein the bilayered lipid mixture consist of phospholipid and cholesterol.

5. The product of claim 2 wherein the bilayered lipid mixture consist of phospholipid and cholesterol, and the additional charged lipid is a (lipophilic) amphipathic compound.

6. The product of claim 2 wherein the phospholipid is selected from the group consisting of a phosphatidylcholine derivative, a glycerophosphatide, a lysophosphatide, sphingomyclin, and mixtures thereof.

7. The product of claim 2 wherein the amphipathic compound is selected from the group consisting of a dialkyl phosphate, a phosphatidic acid and a phosphatidyl serine.

8. The product of claim 5 wherein the amphipathic compound is selected from the group consisting of dicetyl phosphate, dilauryl phosphate, stearylamine and hexadecylamine.

9. The product of claim 5 wherein the anti-leishmanial 8-aminoquinoline drug is primaquine.

10. The product of claim 5 wherein the anti-leishmanial 8-aminoquinoline drug is 8-(6-diethylaminohexylamino)-6-methoxylepidine.

11. A method for treating leishmaniasis which comprises the step of administering parenterally or orally to an infected animal a leishmanicidally effective amount of an anti-leishmanial 8-aminoquinoline drug encapsulated within liposomes prepared in accordance with claim 1.

12. The method of claim 11 wherein the encapsulated anti-leishmanial 8-aminoquinoline drug is prepared in accordance with claim 5.

13. The method of claim 11 wherein the encapsulated anti-leishmanial 8-aminoquinoline drug is prepared in accordance with claim 6.

14. The method of claim 11 wherein the encapsulated anti-leishmanial 8-aminoquinoline drug is prepared in accordance with claim 7.

15. The method of claim 11 wherein the encapsulated anti-leishmanial 8-aminoquinoline drug is prepared in accordance with claim 8.

16. The method of claim 11 wherein the encapsulated anti-leishmanial 8-aminoquinoline drug is primaquine.

17. The method of claim 11 wherein the encapsulated anti-leishmanial 8-aminoquinoline drug is 8-(6-diethylaminohexylamino)-6-methoxylepidine.

* * * * *